Figure 1:
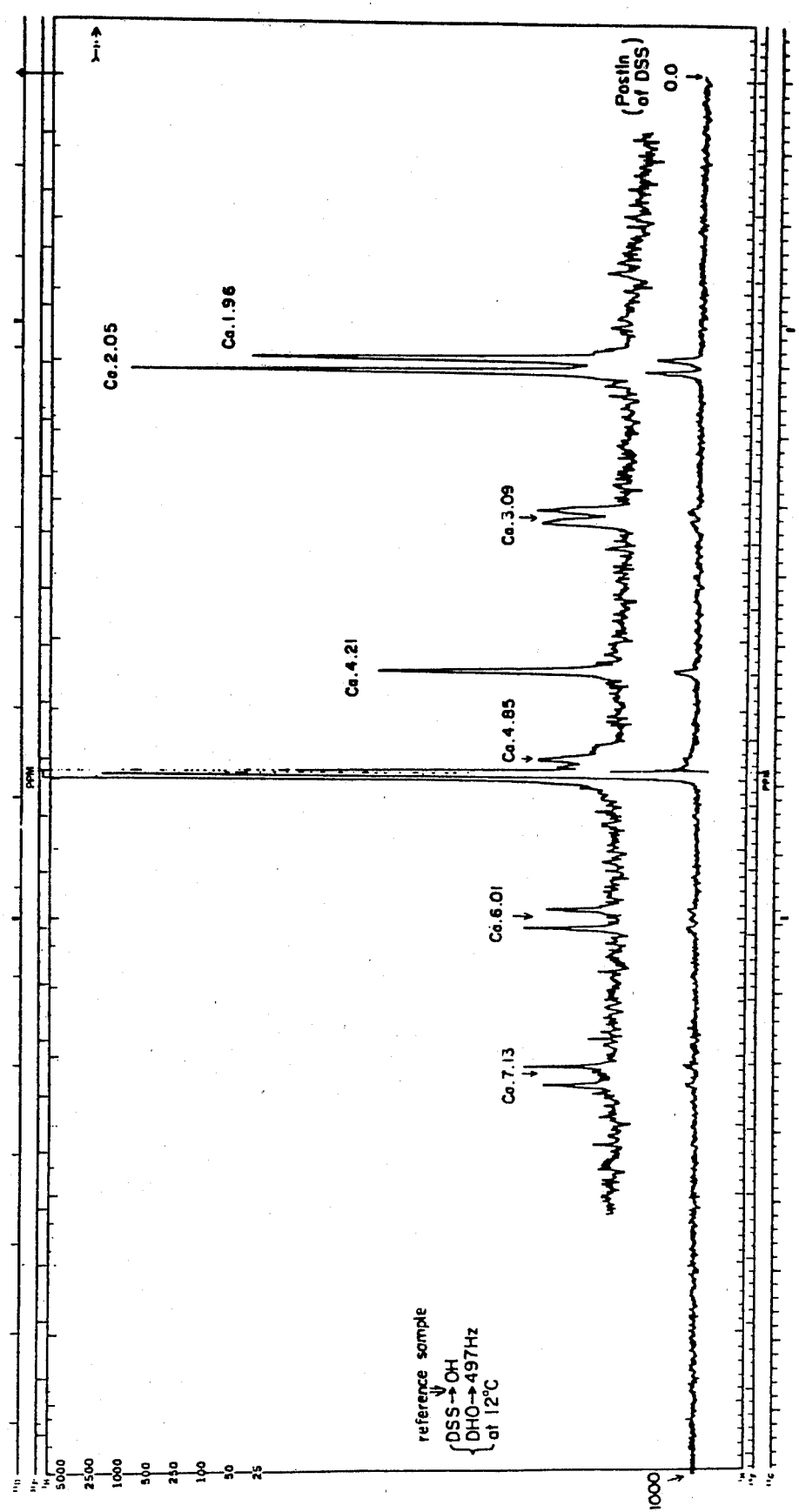

United States Patent [19]

Tanaka et al.

[11] 4,387,052
[45] Jun. 7, 1983

[54] ANTIBIOTIC PA-39504-X$_3$ AND PRODUCTION THEREOF

[75] Inventors: Kentaro Tanaka, Suita; Eiji Kondo, Ikeda; Kouichi Matsumoto, Toyonaka; Jun'ichi Shoji, Hirakata; Naoki Tsuji, Ashiya, all of Japan

[73] Assignee: Shionogi & Co., Ltd., Osaka, Japan

[21] Appl. No.: 286,757

[22] Filed: Jul. 27, 1981

[30] Foreign Application Priority Data

Aug. 25, 1980 [JP]  Japan ................................ 55-117182

[51] Int. Cl.$^3$ .................... C07D 487/04; A61K 31/40
[52] U.S. Cl. ............................. 260/245.2 T; 424/274; 435/119
[58] Field of Search ................... 260/245.2 T

[56] References Cited

U.S. PATENT DOCUMENTS 4,292,241  9/1981  Tanaka et al. ............... 260/245.2 T

FOREIGN PATENT DOCUMENTS 2042532  9/1980  United Kingdom ......... 260/245.2 T

OTHER PUBLICATIONS

Prasad et al.; Heterocycles vol. 16, No. 8, pp. 1305–1309, (1981).

*Primary Examiner*—Mary C. Lee
*Attorney, Agent, or Firm*—Wenderoth, Lind & Ponack

[57] ABSTRACT

A new antibiotic having β-lactamase inhibitory activity, PA-39504-X$_3$ of the formula:

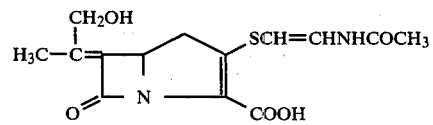

and the pharmaceutically acceptable slats being useful as a drug, a animal drug and a disinfectant for inhibiting the growth of gram-positive and gram-negative pathogenic microorganisms and a process for preparing the same, being characterized by cultivating *Streptomyces argenteolus* PA-39504 or *Streptomyces tokunonensis* PA-31088 in a suitable medium and isolating PA-39504-X$_3$ from the cultured broth.

2 Claims, 1 Drawing Figure

ANTIBIOTIC PA-39504-$X_3$ AND PRODUCTION THEREOF

The present invention relates to a new antibiotic PA-39504-$X_3$ and a process for producing it.

The antibiotic PA-39504-$X_3$ and its pharmaceutically acceptable salts of the present invention are new and useful antibiotics which have a broad antibacterial spectrum and a $\beta$-lactamase inhibiting activity.

PA-39504-$X_3$ has the following structural formula.

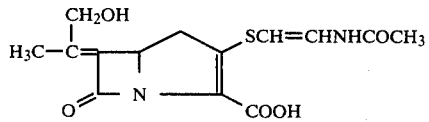

The present invention includes the above compound PA-39504-$X_3$ and its pharmaceutically acceptable salts. As the salts, the salts with alkali metal (such as sodium, potassium) and alkaline earth metal (such as calcium, barium) are exemplified.

The sodium salt of PA-39504-$X_3$ has the following physical and chemical properties.

(a) Ultraviolet absorption spectrum: $\lambda_{max}^{H2O}$ ($E_1$ $cm^{1\%}$) nm 234(680), 296(316).

(b) Nuclear magnetic resonance spectrum (FIG. 1) $\delta_{ppm}^{D2O}$ (J=Hz) 1.96s3H, 2.05s3H, 3.09m2H, 4.21s2H, 4.85 m, 6.01d1H (8.4), 7.13d1H (8.4).

(c) Circular dichroism spectrum: $\lambda_{nm}[\theta]$ 425(0), 350(−2540), 332(−2190), 279(−10600), 263(0), 258(+3030), 252(0), 238(−10900), 224(0), 216.5(+8200), 211(+6060), 200(+23300).

(d) Mass spectrum (Filed desorption mass spectrum) M/z 459=[$M^{30}$] (measured as p-nitrobenzyl ester)

In the prior art, epithienamycins and olivanic acids have been known as carbapenem type antibiotics having a $\beta$-lactamase inhibiting activity. (P. G. Sammes: Topics in Antibiotic Chemistry, volume 3, 118–123). These compounds, however, are different from PA-39504-$X_3$ of the present invention in that the substituent of the 6 position is 1-hydroxyethyl, while it is hydroxymethyl ethylidene in the compound of the present invention. In this connection, the inventors have found previously that Streptomyces sp. PA-39504 produces PA-39504-$X_1$ (Jap. Pat. Application No. 54-161170). This compound, however, has a saturated acetylaminoethylthio group as a side chain at the 3 position, in which respect the compound in the present invention is different from the compound PA-39504-$X_1$. Moreover, PA-31088-IV, an antibiotic produced by Streptomyces tokunonensis PA-31088 (Jap. Pat. Application No. 54-42347, Jap. Pat. OPI No. 13682/80) is different from the compound in the present invention in view of the point that this compound has a sulfoxide on the side chain at the 3 position instead of the sulfide. PA-39504-$X_3$ is produced by the aforementioned organism Streptomyces sp. PA-39504 and Streptomyces tokunonensis PA-31088. The former has been described in Jap. Pat. Application No. 54-161170 as an organism producing PA-39504-$X_1$ with its bacteriological properties. The strain has been deposited in Agency of Industrial Science & Technology (Yatabe-machi, Tukuba-gun, Ibaragi Pref.) since November 1st, 1979 as FERM-P No. 5265 and in the American Type Culture Collection (Parklawn Drive, Rockville, Maryland) as ATCC No. 31589. The later has been described in Jap. Pat. OPI No. 136282/80 as an organism producing PA-31088-IV with its bacteriological properties. The type culture has been deposited in Agency of Industrial Science & Technology since Feb. 26, 1979 as FERM-P No. 4843, and in the American Type Culture Collection as ATCC No. 31569.

Additionally, it was concluded afterwards that the strain PA-39504 belongs to Streptomyces argenteolus from the results of bacteriological experiments and the strain is designated Streptomyces argenteolus PA-39504.

The bacteriological properties of the strains PA-39504 and PA-31088 are characterized as follows.

1. Streptomyces sp. PA-39504

(a) Morphological properties (Bennett's agar, 28° C., cultured for 14 days)

This strain grows well on Bennett's agar, and forms aerial hyphae abundantly. The aerial hyphae branch simply, of which the terminal forms loop or short spiral. The color of aerial hyphae on the above agar medium is light brownish grey to brownish grey, and that of substrate hyphae is pale yellowish brown. No soluble pigment is produced. The surface structure of the spore is smooth and the spore is short cylindrical as observed under an electron microscope. Neither sporangium, flagellated spore nor selerotium is observed, and no split by fragmentation is observed on the substrate hyphae.

(b) Physiological properties

| | |
|---|---|
| Liquefaction of gelatin | negative |
| Production of melanoid pigment | negative |
| Tyrosinase reaction | negative |
| Peptonization of milk | positive |
| Coagulation of milk | negative |
| Hydrolysis of starch | positive |

(c) Utilization of sugar
Favourable in growth by:
L-arabinose, D-xylose, D-glucose, D-fructose, inositol, L-rhamnose
No growth observed:
sucrose, raffinose, D-mannitol (d) Growth temperature

| | |
|---|---|
| 10° C. | Appreciable growth forming scarcely aerial hyphae |
| 28° C. | Favourable growth abundant in aerial hyphae |
| 37° C. | No growth |
| 45° C. | No growth |

2. Streptomyces tokunonensis PA-31088

(a) Morphological properties (Bennett's agar, 28° C., cultured for 14 days)

Neither sporangium, flagellated spore nor selerotium is observed, and no split by fragmentation of substrate hyphae is observed. Aerial hyphae are formed abundantly on the above agar medium. Spore-bearing hyphae are attached to the aerial hyphae, from which simple branches are spread as side branches with spiral terminals. The surface structure of the spore is smooth and the spore is short cylindrical as observed under an electron microscope.

(b) Properties on medium (28° C., cultured for 14 days)

| Medium | Growth | Aerial Hyphae Formation | Aerial Hyphae Color | Color of Substrate Hyphae | Soluble Pigment |
|---|---|---|---|---|---|
| Sucrose.Nitrate Agar | fair | fair | pale brown | pale yellowish brown | none |
| Glucose.Asparagine Agar | fair | none | — | pale yellowish brown | none |
| Glycerin.Asparagine Agar | fair | slightly | white | pale yellowish brown | none |
| Inorganic salt.Starch Agar | good | good | pale reddish orange | pale yellowish brown | none |
| Tyrosine Agar | good | fair | pale brown | pale yellowish brown | none |
| Nutrient Agar | fair | none | — | pale yellowish brown | none |
| Yeast extract.Malt extract Agar | good | good | pale reddish orange | plae yellowish brown | none |
| Oatmeal Agar | good | good | pale reddish orange | pale yellowish brown | none |
| Bennett's Agar | good | good | pale reddish orange | pale yellowish brown | none |

The expression of color is given by "Guide to Color Standard" (Japan Color Institute ed.).

(c) Physiological properties

| | |
|---|---|
| Liquefaction of gelatin | poor growth |
| Production of melanoid pigment | negative |
| Tyrosinase reaction | negative |
| Peptonization of milk | positive |
| Coagulation of milk | negative |
| Hydrolysis of starch | positive |

(d) Utilization of sugar
  Favourable in growth by:
  D-glucose, inositol
  No growth observed:
  L-arabinose, D-xylose, D-fructose, sucrose, L-rhamnose, raffinose, D-mannitol
(e) Growth temperature

| | |
|---|---|
| 10° C. | No growth |
| 28° C. | Favourable growth, abundant in aerial hyphae |
| 37° C. | Considerable growth forming no aerial hyphae and no spore |
| 42° C. | No growth |
| 45° C. | No growth |
| 50° C. | No growth |

All of the PA-39504-$X_3$ producing strains of Streptomyces are utilized and included in the present invention, as well as the above mentioned strains PA-39504 and PA-31088 and their natural and artificial variants.

A fermentative process for producing PA-39504-$X_3$ is shown as follows. A PA-39504-$X_3$ producing strain is cultured on a neutrient medium under aerobic condition, and after termination of the culture, PA-39504-$X_3$ is recovered from the culture broth.

In this fermentation, conventional medium components and conditions can be utilized. The medium includes substantially carbon sources, nitrogen sources, and inorganic salts. If necessary, vitamines, precursors, and other components can be added to increase the yield of PA-39504-$X_3$. As carbon sources, for example, glucose, starch, dextrin, glycerin, molasses, organic acid, etc. are used alone or as a mixture. As nitrogen sources, for example, soybean meal, corn steep liquor, meat extract, yeast extract, cotton seed meal, peptone, wheat embryo, ammonium sulfate, ammonium nitrate, etc. are used alone or as a mixture. As inorganic salts, for example, calcium carbonate, sodium chloride, potassium chloride, magnesium sulfate, cobaltous chloride, various salts of phosphoric acid, if necessary, may be added to the medium.

The culture may be made according to the method generally used for antibiotics, and in case of liquid culture, particularly in a large scale production, it may be effected under submerged aerial conditions. Favourable pH in the medium is about 5.5–8.5, and if the pH range in the medium varies during the production, a buffer such as calcium carbonate may be added to the medium. The culture is preferably conducted at about 20°–40° C., particularly 25°–32° C. Although the culture time largely depends on the scale of fermentation, it usually takes about 20–80 hours in large scale productions. If a violent bubbling occurs during the culture, defoamers such as vegetable oil, lard, polypropylene glycol may be added before or during the culture.

After termination of the culture, PA-39504-$X_3$ is recovered from the culture broth by the conventional method for recovering usual fermentation products. For example, filtration, centrifugation, adsorption-desorption procedure or chromatography, with various ion exchange resins or the other active adsorbents, extraction with various organic solvents, etc. can be employed in suitable combination. If necessary, any proper stabilizer may be added during the separation process to prevent PA-39504-$X_3$ from decomposition.

If PA-39504-$X_3$ is produced with PA-39504-$X_1$ concurrently, PA-39504-$X_3$ can be separated from PA-39504-$X_1$ by chromatography using an ion exchange resin with properly combined eluting solvents. Moreover, PA-39504-$X_3$ can be separated as a salt for the purpose of purification.

The antibiotic, PA-39504-$X_3$ in the present invention can be produced also by means of chemical syntheses. For example, PA-39504-$X_3$ can be produced by disoxidating PA-31088-IV (Jap. Pat. OPI No. 136,282/80) which corresponds to the sulfoxide of PA-39504-$X_3$.

In disoxidating PA-31088-IV, a mild condition which has no influence on the other functional groups is employed. For example, reflux with triphenylphosphine in carbon tetrachloride, reaction with titanium trichloride, formation of an alkoxysulfonium salt followed by reduction with a borohydride or cyanogen borohydride, reaction with chromous chloride (Y. Akita et al.: Synthesis, 1977, 792), reaction with phosphorous pentoxide (I. W. J. Still et al.: Synthesis, 1977, 468), reaction with trifluoroacetic anhydride and hydrogen sulfide (J. Drabowicz et al.: Chem. Letters, 1977, 767) can be utilized in suitable conditions.

PA-39504-$X_3$ has an activity against gram positive and gram negative bacteria, and a β-lactamase inhibiting activity. The following indicate the antibacterial spectrum of PA-39504-$X_3$ and antimicrobial activities against cephalosporinase type and penicillinase type β-lactamase producing organisms.

| Organism tested | Minimum Growth Inhibitory Concentration (μg/ml) |
|---|---|
| 1. Antibacterial spectrum | |
| Staphylococcus aureus 209P JC-1 | 6.3 |
| Streptococcus pyogenes C-203 | 0.8 |
| Escherichia coli NIHJ JC-2 | 0.8 |
| Klebsiella pneumoniae SRL-1 | 0.8 |
| Klebsiella sp. 363 (P) | 0.8 |
| Proteus mirabilis PR-4 | 1.6 |
| Proteus vulgaris CN-329 | 1.6 |
| Enterobactor cloacae 233 | 1.6 |
| Pseudomonas aeruginosa ATCC 25619 | 25 |
| 2. Antimicrobial activities against β-lactamase producing strains | |
| Escherichia coli 6 | 0.031 |
| Proteus morganii | 1 |
| Proteus inconstans 31 | 0.125 |
| Enterobactor cloacae 92 | 0.5 |
| Proteus vulgaris 31 | 0.25 |
| Klebsiella sp. 363 | 8 |
| Enterobactor cloacae 53 | 2 |
| Escherichia coli RTEM | 0.5 |
| Escherichia coli RGN 238 | 2 |

Note:
Cephalosporinase type β-lactamase producing strains and pencillinase type β-lactamase producing strains are shown in the upper and lower columns, respectively.

As shown in the above table, PA-39504-$X_3$ has an activity against gram positive and gram negative bacteria, and particularly it is effective against β-lactamase producing organisms. Thus, PA-39504-$X_3$ is useful as a drug, an animal drug, and a disinfectant. PA-39504-$X_3$ and its pharmaceutically acceptable salts are administered orally or parenterally to humans and animals. They may be administered orally in the forms of tablets, capsules, powders, etc. together with excipients, stabilizers, preservatives, wetting agents, surfactants and so on, or patenterally as injection, liniment, or suppositories. The dosage of PA-39504-$X_3$ is variable according to therapeutic purposes, and in general it is effective at 1/10-several times the dosage of cephalothin; for example, it may be administered subcutaneously at a dose of 0.1-30 g a day for an adult.

Moreover, PA-39504-$X_3$ has a potent β-lactamase inhibiting activity, so it can increase synergistically anti-microbial activities of β-lactam antibiotics against β-lactamase producing organisms. Accordingly PA-39504-$X_3$ can be used together with known β-lactam antibiotics such as penicillin antibiotics (benzylpenicillin, phenoxymethyl penicillin, carbenicillin, ampicillin, amoxicillin, etc.) and cephalosporin antibiotics (cephaloridine, cephalothin, cefazolin, cephalexin, cefoxitin, cephacetrile, cefamandole, cephapirin, cepharadine, cephaloglycin, ceftezole, cefatrizine, cefmetazole, etc.).

The following show examples of producing PA-39504-$X_3$, the objective compound in the present invention. The following examples, however, are not intended to limit the scope of the present invention.

EXAMPLE 1

Seed culture of Streptomyces argenteolus PA-39504 (FERM-P No. 5265, ATCC No. 31589) is inoculated on 100 ml of a medium consisting of soluble starch (0.5%), glucose (0.5%), polypeptone (0.5%), meat extract(0.5%), yeast extract (0.25%), sodium chloride (0.25%), deionized water (pH 7.0), placed in a 500 ml Sakaguchi's flask, and cultured with shaking at a rate of 140 strokes per minute at 28° C. for 48 hours. Four ml of the culture broth is transplanted on 100 ml of a medium consisting of dextrin (2%), yeast extract (1%), tomato paste (2%), cobalt chloride (0.0005%), placed in a Sakaguchi's flask, and cultured with shaking at 28° C. for 72 hours.

(b) Separation process

The culture broth obtained in the above procedure is filtrated through Hyflosupercell (Trade Mark). The filtrate (800 ml) is cooled to 10° C., adjusted at pH 7.0, passed through a Dowex 1×2 column (Cl$^-$type)(100 ml) (Dow Chemical Co., U.S.A.) at a flow rate of 10 ml per minute, and eluted with 3% sodium chloride in cold deionized water to give a PA-39504-$X_1$ fraction followed by elution with 3% sodium chloride in 50% methanol. The fractions (400 ml) that are positive to E.coli in the pulp disc diffusion method are collected, adjusted at pH 7.0, and evaporated under reduced pressure to 150 ml. Then the resulting solution is applied to a 150 ml Daiaion HP-20 column (Mitsubishi Chemical Industries Co.) and eluted at a flow rate of 10 ml per minute. An antimicrobially active fraction is eluted with water, followed by elution with cold deionized water containing 25% methanol to collect 50 ml of the another active fraction. The latter fraction is adjusted to pH 7.0, and then freeze-dried to give 15 mg of PA-39504-$X_3$ as crude powder.

The powder (15 mg) is dissolved in a 5% methanol-0.05 M sodium dihydrogenphosphate buffer (pH 7.0), applied to high-performance liquid chromatography using a Nucleosil-5-$C_8$ column (10 mm×30 cm) with the above buffer. The active fraction is desalted and then freeze-dried. The resulting powder is applied to high-performance liquid chromatography using a Nucleosil-7-$C_{18}$ column (10 mm×30 cm) with a 10% methanol-0.05 M sodium dihydrogenphosphate buffer (pH 7.0), desalted, and freeze-dried to give PA-39504-$X_3$ as amorphous powder.

In order to obtain the same objective compound, the above fermentation and purification process can also be achieved with Streptomyces tokunonensis PA-31088 (FERM-P No. 4843, ATCC No. 31569) instead of Streptomyces argenteolus PA-39504 used in the above.

EXAMPLE 2

To 26 mg of titanium trichloride is added 26 ml of 0.5 M acetic acid-sodium acetate buffer (pH 7.0), and a solution of 20 mg of PA-31088-IV in 4 ml of the above buffer is added thereto with stirring in nitrogen atomosphere at room temperature. Ten minutes later, the reaction mixture is adsorbed on a 7 ml Daiaion HP-20AG column (Mitsubishi Chemical Industries Co.) preliminarily treated with 5% sodium chloride-0.05 M phosphorate buffer, and after washing with 60 ml of the above buffer, eluted with water at a flow rate of 3 ml per minute. The antimicrobially active fraction (43 ml) is evaporated to about 3 ml under reduced pressure, adsorbed on a 18 ml Daiaion HP-20AG column preliminarily treated with water, and eluted with water. The resulting active fraction (28 ml) is evaporated under reduced pressure to about 2 ml, and then dried to give 5 mg of PA-39504-$X_3$ sodium salt as light yellow powder.

What is claimed is:

1. Antibiotic PA-39504-X₃ of the formula:

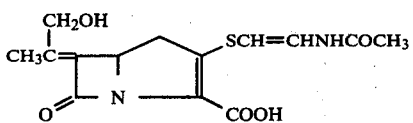

or a pharmaceutically acceptable salt thereof.

2. The antibiotic claimed in claim 1, of which the sodium salt has the following properties:

(a) Ultraviolet absorption spectrum: $\lambda_{max}^{H2O}$ ($E_1$ $cm^{1\%}$) nm 234(680), 296(316)

(b) Nuclear magnetic resonance spectrum: $\delta_{ppm}^{D2O}$ (J=Hz) 1.96s3H, 2.05s3H, 3.09m2H, 4.21s2H, 4.85 m, 6.01d1H (8.4), 7.13d1H (8.4)

(c) Circular dichroism spectrum : $\lambda_{nm}[\theta]$425(0), 350(−2540), 332(−2190), 279(−10600), 263(0), 258(+3030), 252(0), 238(−10900), 224(0), 216.5(+8200), 211(+6060), 200(23300)

(d) Mass spectrum (Field desorption mass spectrum) M/z 459=[M⁺] (measured as p- nitrobenzyl ester).

* * * * *